(12) United States Patent
Guth et al.

(10) Patent No.: US 7,493,793 B2
(45) Date of Patent: *Feb. 24, 2009

(54) BREATH TEST SIMULATOR

(76) Inventors: Richard U. Guth, 439 N. 46th St., Harrisburg, PA (US) 17111; David A. Fisher, 610 S. 20th St., Harrisburg, PA (US) 17104

( * ) Notice: Subject to any disclaimer, the term of this patent is extended or adjusted under 35 U.S.C. 154(b) by 0 days.

This patent is subject to a terminal disclaimer.

(21) Appl. No.: 11/844,461

(22) Filed: Aug. 24, 2007

(65) Prior Publication Data

US 2008/0060409 A1    Mar. 13, 2008

Related U.S. Application Data

(63) Continuation-in-part of application No. 11/530,489, filed on Sep. 11, 2006, now Pat. No. 7,404,311.

(51) Int. Cl.
G01N 33/497 (2006.01)
G01N 1/22 (2006.01)
G12B 13/00 (2006.01)
G01C 25/00 (2006.01)

(52) U.S. Cl. .......... 73/1.03; 73/23.3; 73/23.34; 73/863.11; 73/863.81; 422/83; 422/84; 436/9

(58) Field of Classification Search .......... 73/1.03, 73/1.04, 1.06, 23.3, 23.34, 863.11, 863.81; 422/83, 84, 85; 436/9
See application file for complete search history.

(56) References Cited

U.S. PATENT DOCUMENTS

| | | | |
|---|---|---|---|
| 3,520,194 A | 7/1970 | Adams | |
| 3,552,930 A * | 1/1971 | Borkenstein | 422/85 |
| 3,853,477 A * | 12/1974 | Block et al. | 422/85 |
| 3,854,319 A | 12/1974 | Burroughs et al. | |
| 3,854,320 A * | 12/1974 | Burroughs et al. | 73/23.3 |
| 3,904,849 A | 9/1975 | Lucero et al. | |
| 3,948,604 A * | 4/1976 | Hoppesch | 422/84 |
| 3,982,095 A | 9/1976 | Robinson | |
| 4,003,240 A | 1/1977 | Durbin | |
| 4,009,713 A | 3/1977 | Simmons et al. | |
| 4,028,444 A | 6/1977 | Brown et al. | |
| 4,028,445 A | 6/1977 | Hickmann et al. | |
| 4,036,915 A | 7/1977 | Lucero et al. | |
| 4,036,919 A | 7/1977 | Komendowski et al. | |
| 4,101,611 A | 7/1978 | Williams | |
| 4,407,152 A | 10/1983 | Guth | |
| 4,412,526 A * | 11/1983 | DeGrose | 122/14.1 |
| 4,474,048 A | 10/1984 | Schmidt | |
| 4,567,748 A | 2/1986 | Klass et al. | |
| D291,355 S * | 8/1987 | Stanuch et al. | D24/169 |
| 5,134,875 A * | 8/1992 | Jensen et al. | 73/1.03 |
| 5,731,508 A | 3/1998 | Slemeyer | |
| 6,526,802 B1 | 3/2003 | Fisher et al. | |
| 6,770,482 B1 * | 8/2004 | Flanagan et al. | 436/37 |
| 7,422,723 B1 * | 9/2008 | Betsill | 422/84 |
| 2004/0138823 A1 * | 7/2004 | Gollar | 702/19 |
| 2004/0236244 A1 * | 11/2004 | Allen et al. | 600/532 |
| 2005/0232074 A1 * | 10/2005 | Higashihara et al. | 366/273 |

* cited by examiner

*Primary Examiner*—David A. Rogers
(74) *Attorney, Agent, or Firm*—Hooker & Habib, P.C.

(57) ABSTRACT

A breath simulator for supplying a breath test analyzer with a sample effluent of ethyl alcohol that controls headspace and adjacent effluent passageway temperature.

16 Claims, 3 Drawing Sheets

BREATH TEST SIMULATOR

This application is a Continuation-In-Part of our application for "Breath Test Simulator" filed Sep. 11, 2006, Ser. No. 11/530,489, now U.S. Pat. No. 7,404,311.

FIELD OF THE INVENTION

The invention relates to breath simulators that supply sample effluent containing a precisely controlled concentration of ethyl alcohol to a breath test analyzer for calibrating the analyzer.

DESCRIPTION OF THE PRIOR ART

The alcohol content in the breath of an individual is an indicator of the alcohol content in the blood of the individual. Breath test analyzers are commonly used to determine the alcohol content in the blood of an individual, typically the driver of a motor vehicle, by determining the alcohol content in the breath of the individual.

Breath test analyzers must be calibrated to maintain accuracy. A known means of calibrating an analyzer is to use a breath test simulator that flows air through a solution of water and ethyl alcohol of known concentration heated to an operating temperature to generate a breath test effluent sample having a known alcohol concentration. The effluent sample is flowed to an analyzer to calibrate the analyzer. Breath test simulators must provide breath test effluent samples having precisely controlled ethyl alcohol concentrations in order to calibrate breath test analyzers accurately.

Breath test simulators of the type disclosed in Fisher et al. U.S. Pat. No. 6,526,802 are manufactured by Guth Laboratories, Inc. of Harrisburg, Pa. These simulators include a jar sealed closed by a lid and containing a water-alcohol solution of known alcohol concentration and an effluent headspace over the solution. An immersion heater heats the solution to a desired operating temperature, typically 34° C., while a stirrer circulates the solution to assure even heating. An immersion sensor in the solution monitors the temperature of the solution. When the solution is at the desired operating temperature, outside air is bubbled through the solution. Air bubbled through the solution absorbs a known amount of ethyl alcohol from the solution and is collected in the headspace above the solution. The gas in the headspace includes air, water vapor and alcohol vapor. Headspace gas effluent is flowed from the headspace to a breath test analyzer to calibrate the analyzer.

Samples of headspace gas flowed to analyzers for calibrating the analyzers must have a known concentration of ethyl alcohol. This concentration may vary slightly within an acceptable range. More accurate control of the concentration of ethyl alcohol in the breath test sample is desirable and permits calibrating the analyzer more accurately so that the analyzer conducts breath tests with improved accuracy.

In known breath test simulators, headspace temperature is primarily dependent on the temperature of the water-alcohol solution below the headspace. As air is bubbled through the heated solution to form the headspace gas, headspace temperature decreases due to evaporation and the cooler temperature of air. The heater immersed in the solution does not directly heat the gas in the headspace to compensate for this temperature drop. The gas may be heated slightly by incidental heat given off by electric components mounted on the lid or on the body of the simulator. This heat does not compensate for the heat loss.

The temperature of the headspace gas produced by the simulator and the alcohol concentration in the gas would be more accurately controlled by heating the air and vapor in the headspace to the operating temperature and maintaining the air and vapor at the operating temperature.

Breath test effluent from the headspace passes through an outlet passage leading to the analyzer. Heat loss in the passage can effect the alcohol concentration in the effluent and can cause condensation. Calibration accuracy of simulators would be improved by heating the outlet passage to maintain the temperature of the effluent and prevent condensation.

Breath test simulator Model 2100 marketed by Guth Laboratories, Inc. of Harrisburg, Pa. uses a sealed jar containing a known concentration water-alcohol solution and has a headspace over the solution. A cap closes the jar at the top of the headspace and supports an immersion heater extending into the solution and an electric motor which rotates a stirrer extending into the solution. The lid also supports an immersion sensor for monitoring the temperature of the solution and an air inlet for flowing air into the solution. Effluent from the headspace is flowed to a breath test analyzer to calibrate the analyzer. Electrical components are mounted on the lid. During operation of the simulator incidental heat from these components does not compensate for heat loss.

Conventional simulators are not capable of rapid warm up heating of the solution and headspace gas from ambient temperature to an operating temperature of 34° C. and rapid stabilization of the solution and headspace gas at the desired operating temperature within 10 minutes of activation. Operators are required to wait for a considerably longer period of time before stabilization occurs and the simulator is ready to be used to calibrate breath test analyzers. In some cases, a warm up period of 35 to 40 minutes is required.

Long warm up periods are undesirable. Operator time is wasted. The simulators may be powered by a battery. In such a case, a long warm up time unduly discharges the battery and wastes energy.

Therefore, there is a need for a breath test simulator that quickly warms up to an operating temperature and then precisely controls headspace temperature to allow stabilized generation of breath test effluent having a known concentration of ethyl alcohol.

SUMMARY OF THE INVENTION

The invention is a breath test simulator with an improved headspace heater for rapid warm up and controlled maintenance of the temperature of the headspace gas.

The simulator has a sealed jar containing an ethyl alcohol-water solution of known concentration and a headspace over the solution. An immersion heater heats the solution to a desired operating temperature and maintains the solution at the temperature. The headspace heater quickly heats and maintains the temperature of gas located in the headspace at the operating temperature. The headspace heater also heats an effluent outlet passage leading to the analyzer.

The simulator includes a black anodized aluminum jar lid heated by a resistor on the lid. A temperature sensor on the lid actuates a switch to flow current through the resistor when the temperature of the lid falls below a low temperature and to stop current flow through the resistor when a high temperature is reached. The resistor heats the lid by conduction so that heat radiates evenly down from the lid into the headspace and heats the gas in the headspace. Heat also radiates up from the lid and heats the effluent outlet passage.

The heaters rapidly warm the solution and the headspace gas to an operating temperature and maintain very precise temperature control of the headspace gas and resultant effluent samples flowed to breath test analyzers to improve the accuracy of analyzer calibration.

Other objects and features of the invention will be apparent as the description proceeds, especially when taken in conjunction with the accompanying drawings illustrating the invention.

DESCRIPTION OF THE PREFERRED EMBODIMENTS

Figure 1:
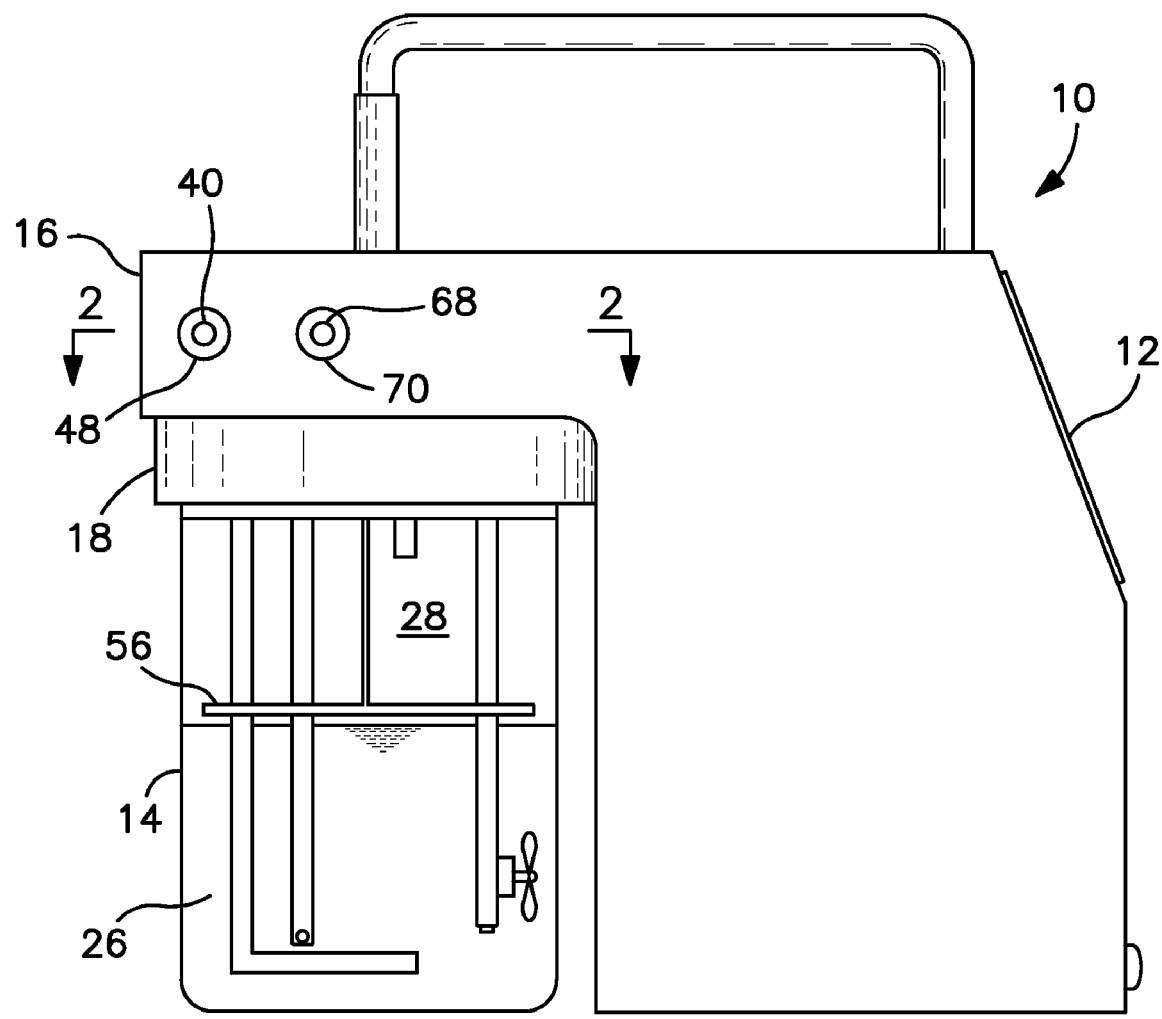
FIG. 1 is a side view of the breath test simulator.
Figure 2:
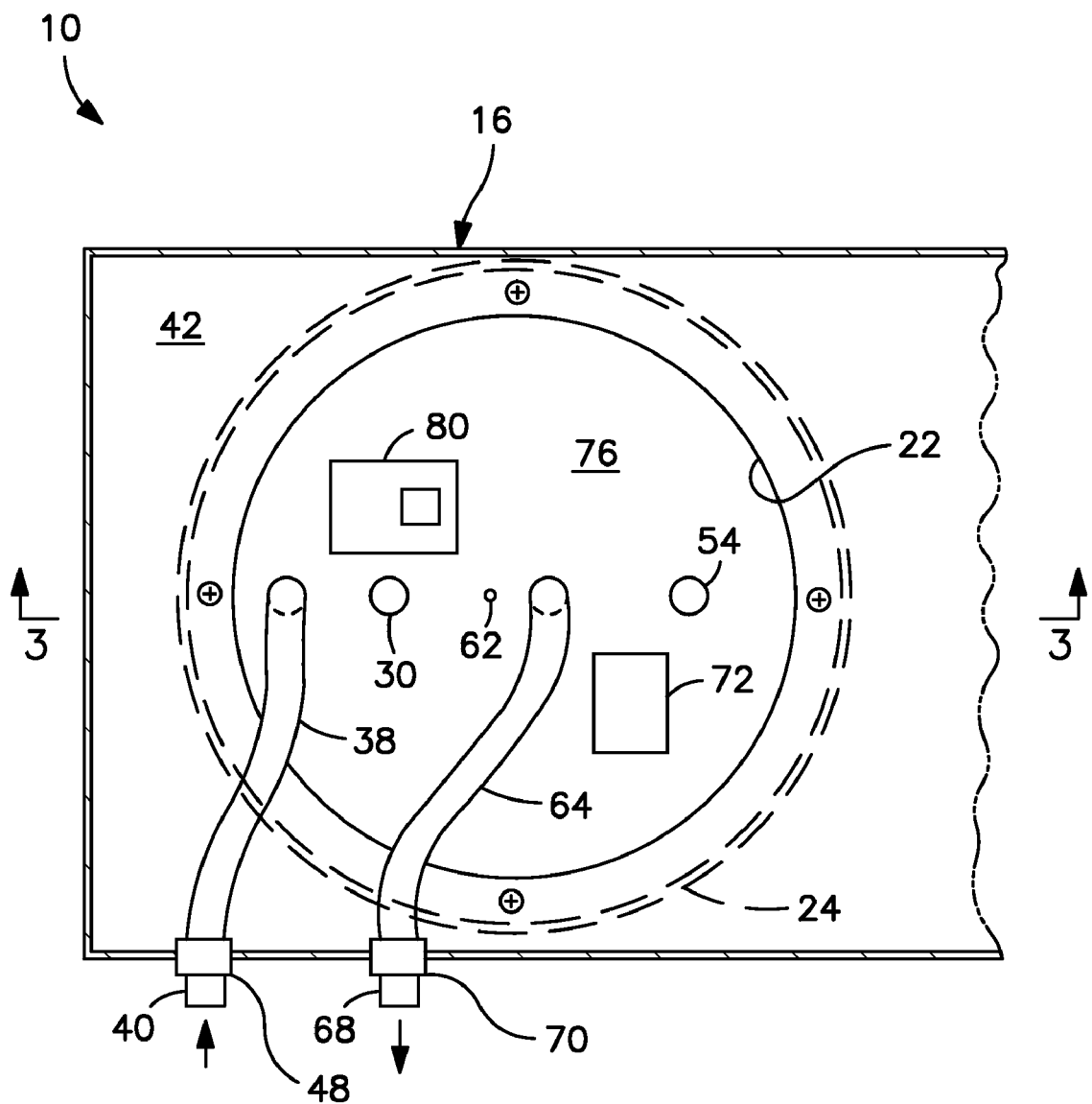
FIG. 2 is a sectional view taken along line 2-2 of FIG. 1.
Figure 3:
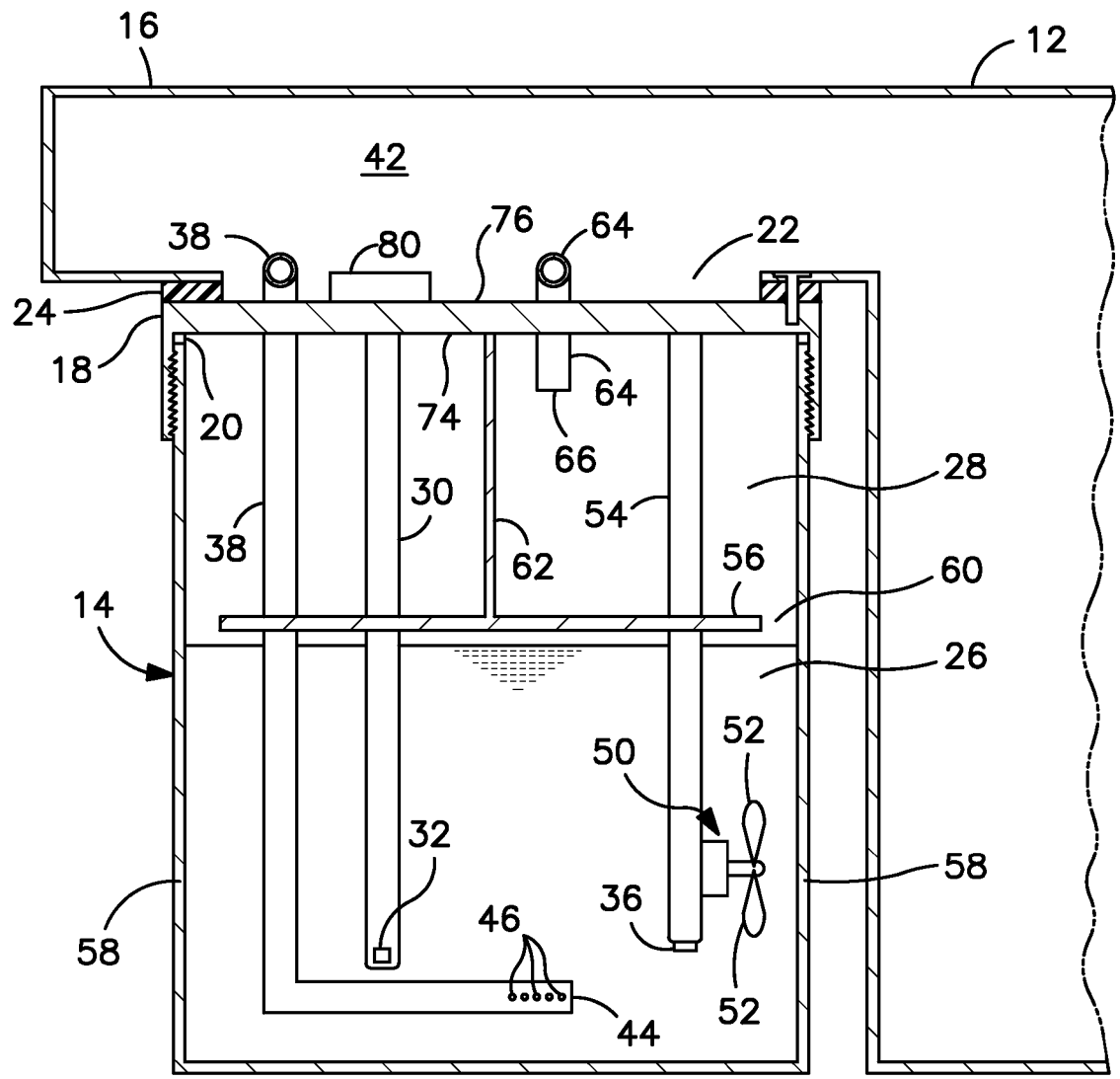
FIG. 3 is a sectional view taken along line 3-3 of FIG. 2.

The breath test simulator 10 disclosed herein relates to the breath test simulator of Fisher et al. U.S. Pat. No. 6,526,802, the disclosure of which is incorporated herein by reference in its entirety.

Portable breath test simulator 10 includes a case or body 12 and a sealed container or jar 14. Jar 14 is mounted on the underside of support arm 16 extending outwardly from one side of body 12. Container 14 may be a plastic jar that is screwed into lid 18 mounted on the underside of support arm 16.

A circumferential gasket 20 is mounted on the lower surface of the lid to engage the top of the jar and prevent leakage into or out from the interior of the chamber 14. Lid 18 is mounted under opening 22 in the lower wall of arm 16. A circumferential thermal gasket 24 is provided between lower wall of the arm and the lid to prevent the lid from heating the arm. Jar 14 is partially filled with an ethyl alcohol-water solution 26 of known concentration. An effluent headspace or chamber 28 in the jar is located above the top of solution 26 and below lid 18.

Arm 16 and lid 18 support a number of components that extend downwardly into jar 14. Immersion heater tube 30 extends through lid 18 and down into the solution in jar 14. Heater tube 30 includes an immersion solution heater 32 at the lower end thereof for heating the solution in the jar. The solution heater may be a resistance heater or other type of heater, including a small halogen light bulb.

Air inlet or blow tube 38 extends from inlet port 40 located to one side of arm 16, though the arm sidewall, through inner arm space 42 and to and down through lid 18 into jar 14. Closed lower end 44 of the blow tube is located in the solution adjacent to the bottom of jar 14. A number of small diameter air dispersion holes or air outlets 46 extend through the immersed end of tube 38 adjacent lower end 44 to disperse air blown through tube 38 and out holes 46 into the alcohol-water solution in the jar. Port 40 is mounted on arm 16 by insulating gasket 48.

Stirrer mechanism 50 is mounted on lid 18 and includes post 54 which extends down into jar 14. The stirrer mechanism includes magnetically actuated stirrer vanes 52 on the immersed end of the post. A magnet is mounted in the outer end of each vane for rotation by a magnetic stirrer drive mounted on body 12 adjacent the jar. Solution temperature sensor 36 is mounted on the lower end of post 54. Alternatively, post 54 may be eliminated and the stirrer mechanism and sensor 36 may be mounted on another component that extends downward into jar 14.

A horizontal baffle plate 56 is located in the jar above the top surface of solution 26 in the bottom of the jar to prevent air bubbled up through the solution from drawing liquid droplets of solution into headspace 28. Heater tube 30, air inlet tube 38 and post 54 extend through openings formed in the baffle plate. The baffle plate is spaced inwardly from the container sidewalls 58 to define a narrow gap 60 between the baffle plate and the sides of the chamber. The baffle plate is supported by post 62 mounted on lid 18.

Air outlet tube 64 extends from effluent inlet end 66 located in the top of effluent headspace 28, through lid 18, through arm space 42, through a sidewall of arm 16 to effluent outlet port 68, mounted in outlet insulating gasket 70 in the sidewall adjacent inlet port 40. The portion of tube 64 extending from lid 18 to port 68 is directly above lid 18.

Electric resistance heater 72 is mounted to the top of lid 18. The heater is in direct contact with the lid to efficiently transmit heat to the lid. Lid lower surface 74 faces headspace 28 and forms a headspace wall. Upper lid surface 76 faces space 42. Lid 18 is formed from heat conductive material, which may be aluminum. Surfaces 74 and 76 are dark and preferably anodized black. Black surface 76 enhances flow of heat from heater 72 into lid 18. Black surfaces 74 and 76 enhance even radiation of heat from lid 18 into headspace 28 and into the arm space 42.

A set point switch control unit 80 includes a temperature sensor on surface 76 and control circuitry for flowing electricity through the resistor 72 when the temperature of the lid falls below an "on" set point temperature and stopping the flow when the temperature of the lid rises to an "off" set point temperature. The "on" set point temperature may be 35.8° C. and the "off" set point temperature may be 36.2° C. The temperature of the lid is maintained between 35.8° C. and 36.2° C. The heated lid maintains the temperature of the breath test gas in the headspace at 34°±0.5° C. Control unit 80 may be part No. DS1620 manufactured by Dallas Semiconductors of Dallas, Tex. The unit 80 is mounted on the upper surface 76 of the lid in direct heat flow contact with the lid.

The aluminum lid may have a thickness of about 0.1 inches and has an appreciable heat sink mass for receiving heat from heater 72 and evenly radiating heat through black surface 74 into the headspace 28 and through black surface 76 into arm space 42. The relatively large mass of thick lid 18 assures that heat is radiated evenly down into the headspace 28 to heat effluent in the headspace. Heat is also radiated upwardly into arm space 42 to heat the portion of air outlet tube 64 in the arm space and heat effluent flowing through tube 64 to heat the effluent and prevent condensation in the tube.

Operation of breath test simulator 10 will now be described.

The breath test simulator and the alcohol solution to be placed in the breath test simulator are typically stored prior to use at an ambient temperature of between 18° C. and 28° C. In order to prepare a simulator for use, it is necessary to remove jar 14 from simulator 12, pour in an appropriate volume of alcohol-water solution into the jar and remount the jar on the simulator. The simulator is then turned on to actuate heaters 32 and 72 and the drive for stirrer 50. The heaters and stirrer are maintained on during a warm up period of about 10 minutes necessary to increase the temperature of solution 26 in the jar and the temperature of the gas in the headspace 28 to a maintained, stable temperature of 34° C.

Heater 32 heats the solution 26 by conduction. Heater 72 heats the lid by conduction. Heat radiates from the lid into the headspace to heat the headspace gas.

Unit 80 flows electricity to heater 72 until the temperature of the lid reaches 36.2° C. and then deactivates the heater. When the temperature of the lid falls to 35.8° C. the heater is reactuated. Maintenance of the lid temperature between 36.2°

C. and 35.8° C. radiates heat into headspace 28 and into arm space 42 to heat both spaces. The heat radiated into headspace 28 heats the headspace gas from initial ambient temperature to the desired operating temperature of 34±0.5° C. in about 10 minutes. The heater 72 heats air space 42 to heat tubes 38 and 64 sufficiently to prevent formation of condensation in the tubes as air and vapor are flowed through the tubes during testing of a breath test analyzer.

Solution in the jar is rapidly warmed up from ambient temperature to a stable operating temperature of 34°±0.05 C in about 10 minutes. Heating and stabilization of the simulator are accelerated by controlled heating of lid 18 and radiant heating of the headspace 28 under the lid.

Rapid heating and stabilization of the simulator within a 10 minute period of time reduces the amount of time required to prepare a simulator for calibration of breath test analyzers. Conventional breath test simulators, including the previously discussed simulators disclosed in U.S. Pat. No. 6,526,802 and Guth Laboratories simulator Model 2100, discussed above, require appreciably longer periods of time to be heated from ambient temperature to an operating temperature of 34° C. The time required to heat a conventional simulator without a controlled, dedicated headspace heater from ambient temperature to a stable operating temperature of 34° C. may be as long as 30-45 minutes. Reduction of the time required to bring the simulator to a stable operating temperature reduces the amount of electricity required during the warm up period, which is significant when the simulator is used to calibrate an analyzer in the field and is powered by a battery.

Simulator 10 may be used to calibrate a breath test analyzer when the solution in jar 14 and the headspace gas reach a stabilized temperatures, as described. Breath test analyzers are calibrated by attaching a blow tube to inlet port 40 on arm 16. The blow tube preferably includes a breath test mouthpiece or trap that captures solids contained in the breath flowed through the tube to prevent solids from entering air inlet tube 38 and 10 clogging dispersion holes 46. The mouthpiece may be of the type disclosed in Guth, U.S. Pat. No. 4,292,978.

A discharge tube is attached to outlet port 68. The other end of the discharge tube is connected to the breath test inlet of the analyzer being tested. The control circuits will cycle the solution heater and the headspace heater on and off through operation of the simulator to maintain effluent samples at the operating temperature as described.

Blowing of outside air into jar 14 increases the pressure in the jar and flows the heated, stabilized headspace gas through outlet tube 64 and to an analyzer being tested. The alcohol in the effluent is measured by the analyzer to generate an analyzer breath alcohol readout. If the readout is high, the analyzer must be adjusted to lower the reading to the known alcohol concentration. If the readout is low, the analyzer must be adjusted to increase the readout. No adjustment is required if the readout is accurate. The simulator may be programmed to produce samples of alcohol effluent having a desired concentration at an operating temperature other than 34° C. The simulator can be programmed to activate the solution heater and headspace heater at variable temperature set points.

In an alternative embodiment, the headspace 28 may be heated by a heater or heaters mounted on the lid and extending down into the headspace. A temperature sensor may be mounted on the bottom of the lid in order to directly sense headspace gas temperature and activate and deactivate the heater or heaters as required to maintain desired headspace temperature. In both embodiments heat is radiated into the headspace by a heated wall defining the headspace. Resistance heater 72 is disclosed. Other types of electrical heaters may be used including halogen lamps.

While we have illustrated and described preferred embodiments of our invention, it is understood that this is capable of modification, and we therefore do not wish to be limited to the precise details set forth, but desire to avail ourselves of such changes and alterations as fall within the purview of the following claims.

What we claim as our invention:

1. A breath test simulator for producing breath test gas having a controlled concentration of ethyl alcohol, the simulator comprising:
    a jar and a lid forming a body defining a chamber;
    a liquid solution in the chamber, the solution comprising water and ethyl alcohol and having a known concentration of ethyl alcohol;
    a headspace in the chamber located above the solution in the chamber;
    a heating member having a heating surface facing the headspace and located above the solution;
    a headspace heater in heat flow engagement with the heating member; and
    a control unit for the heater, wherein
    the control unit includes a switch responsive to a temperature value to activate the heater and deactivate the heater, and is adapted to control the heating member in order to maintain the temperature of gas in the headspace at an operating temperature substantially the same as the temperature of the solution in the chamber.

2. The breath test simulator of claim 1 including an immersion heater located in the liquid solution.

3. The breath test simulator of claim 1 including a temperature sensor on the heating member and a set point controller responsive to the sensor to actuate and deactuate the heater.

4. The breath test simulator of claim 1 wherein the heater heats the heating member to a temperature higher than the temperature of the solution.

5. The simulator of claim 1 including an inlet tube having an air inlet end located outside the chamber, the inlet tube extending from the inlet end into the chamber to an air outlet end in the solution; an effluent outlet tube having an effluent inlet end located in the headspace, the effluent outlet tube extending from the inlet end out of the chamber to an effluent outlet end located outside the chamber.

6. The breath test simulator of claim 5 wherein the outlet tube is proximate the headspace heating member, wherein the heating member heats the outlet tube to heat effluent in the tube.

7. The breath test simulator of claim 1 wherein the lid comprises said heating member.

8. The breath test simulator of claim 7 wherein the heating member is mounted on the lid away from the chamber.

9. The breath test simulator of claim 7 wherein the heating member is aluminum and includes a black heating surface facing the headspace.

10. A breath test simulator for producing breath test gas having a controlled concentration of ethyl alcohol, the simulator comprising:
    a container defining a closed chamber;
    a solution comprising ethyl alcohol in the chamber;
    a headspace in the chamber located above the solution;
    gas in the headspace;
    a blow tube having an inlet end located outside the chamber and an outlet end located in the solution in the chamber;
    an effluent outlet tube having an inlet end located in the headspace and an outlet end located outside the chamber;

a solution heater for heating the solution in the chamber;

a heating member having a heating surface facing the headspace and located above the solution, a headspace heater in heat flow communication with the heating member for heating the effluent in the headspace;

a temperature responsive switch for activating and deactivating the headspace heater;

wherein the solution heater maintains the solution in the chamber at a desired temperature and the headspace heating member maintains the gas in the headspace at a temperature substantially equal to the desired temperature.

11. The breath test simulator of claim 10 wherein the headspace heater maintains the heating member at a temperature greater than the temperature of the headspace gas.

12. The breath test simulator of claim 10 wherein the outlet tube is proximate the headspace heater.

13. A method of producing a breath test gas having a known ethyl alcohol concentration for calibrating a breath test analyzer, comprising the steps of:

A) providing a breath test simulator at an ambient temperature, the simulator having a chamber;

B) placing a water-alcohol solution at an ambient temperature in the chamber with a vapor headspace above the solution in the chamber;

C) heating the solution in the chamber from the ambient temperature to a test temperature of about 34° C. by heating a heater in contact with the solution and flowing heat into the solution by conduction;

D) heating gas in the headspace from the ambient temperature to the test temperature of about 34° C. by heating a wall of the headspace to a temperature greater than the test temperature and radiating heat from the wall into the headspace;

E) flowing gas heated to the test temperature from the headspace to the breath test analyzer; and F) heating both the solution and the gas from the ambient temperature to the test temperature in about 10 minutes from a start time.

14. The method of claim 13 wherein the ambient temperature is about 18° C. to 28° C.

15. The method of claim 13 including the step of:

G) actuating a heater on the wall of the headspace when the temperature of the wall is less than a minimum temperature and deactuating the heater when the temperature of the wall is greater than a maximum temperature, said minimum and maximum temperatures each greater than the test temperature.

16. The method of claim 15 wherein the maximum wall temperature is about 36.2° C. and the minimum wall temperature is about 35.8° C.

* * * * *

UNITED STATES PATENT AND TRADEMARK OFFICE
CERTIFICATE OF CORRECTION

| | |
|---|---|
| PATENT NO. | : 7,493,793 B2 |
| APPLICATION NO. | : 11/844461 |
| DATED | : February 24, 2009 |
| INVENTOR(S) | : Guth et al. |

Page 1 of 1

It is certified that error appears in the above-identified patent and that said Letters Patent is hereby corrected as shown below:

In the Specification:

Column 3, Line 40, replace "Inunersion" with --immersion--.

Signed and Sealed this

Thirty-first Day of March, 2009

JOHN DOLL
*Acting Director of the United States Patent and Trademark Office*